United States Patent
Zuhaier et al.

(10) Patent No.: US 9,011,766 B2
(45) Date of Patent: Apr. 21, 2015

(54) METHOD FOR ENHANCING THE SHELF LIFE OF DONOR BLOOD BY LASER BIOSTIMULATION

(71) Applicant: King Saud University, Riyadh (SA)

(72) Inventors: Al-Khalid Isam Zuhaier, Riyadh (SA); Mohamad Saleh AlSalhi, Riyadh (SA); Vadivel Masilamani, Riyadh (SA)

(73) Assignee: King Saud University, Riyadh (SA)

( * ) Notice: Subject to any disclaimer, the term of this patent is extended or adjusted under 35 U.S.C. 154(b) by 193 days.

(21) Appl. No.: 13/680,199

(22) Filed: Nov. 19, 2012

(65) Prior Publication Data

US 2014/0140889 A1   May 22, 2014

(51) Int. Cl.
  *A61L 2/00* (2006.01)
  *A61L 9/00* (2006.01)
  *B01J 19/00* (2006.01)
  *G01N 23/00* (2006.01)
  *A61N 5/00* (2006.01)
  *B01D 61/00* (2006.01)
  *A01N 1/02* (2006.01)

(52) U.S. Cl.
  CPC .................................. *A01N 1/0294* (2013.01)

(58) Field of Classification Search
  CPC .............................. A01N 1/0294; A61L 2/00
  USPC .......... 422/1, 24, 32, 41, 44, 905; 250/432 R, 250/455.11, 492.1, 559.13; 604/4.01, 5.02, 604/6.07; 210/640, 650, 660, 695
  See application file for complete search history.

(56) References Cited

U.S. PATENT DOCUMENTS

| | | | |
|---|---|---|---|
| 5,030,200 | A | 7/1991 | Judy et al. |
| 5,476,764 | A | 12/1995 | Bitensky |
| 6,814,482 | B2 | 11/2004 | Meyer et al. |
| 7,717,274 | B2 | 5/2010 | Kao et al. |
| 2012/0189711 | A1* | 7/2012 | Greenberg et al. ........... 424/618 |

* cited by examiner

*Primary Examiner* — Monzer R Chorbaji
(74) *Attorney, Agent, or Firm* — Lowe Hauptman & Ham, LLP

(57) ABSTRACT

A method for increasing the shelf life of donor blood contemplates the following steps. In the first step blood is transferred to a sterile container and mixed with an anticoagulant as indicated in step 20. The anticoagulant and donor blood are centrifuged in step 22 at about 4,000 rpm for about 15 minutes. After centrifuging the red blood cells are separated and placed in a sterile tube. In the next step the red blood cells are irradiated by a laser that emanates a wavelength of about 633 nm for a time period of about 24 hours. During rotation the RBCs are rotated to provide uniform exposure. Such laser biostimulation produces an enhancement of shelf life of donor blood by 66%.

6 Claims, 2 Drawing Sheets

METHOD FOR ENHANCING THE SHELF LIFE OF DONOR BLOOD BY LASER BIOSTIMULATION

FIELD OF THE INVENTION

This invention relates to a method for enhancing the shelf life of donor blood. More particularly, the invention relates to a laser bio stimulation for enhancing the shelf life of donor blood.

BACKGROUND FOR THE INVENTION

Red blood cells or erythrocytes are the most common type of red blood cells and the organism's principle means for delivering oxygen to the human body tissue through the bodies' circulatory system. The red blood cells take up oxygen in the lungs and release it while squeezing through the bodies capillaries. Thus, they are a vital part of the human life.

The loss of blood during surgery and as a result of motor vehicle and other accidents, crime, war and natural disasters have created a continuing large demand for donor blood. Therefore, numerous blood banks and donor programs have been established by the Red Cross and other organizations. Nevertheless, there are times, particularly in time of a natural disaster when there are shortages of blood in the region of a disaster.

Another problem associated with donor blood is its shelf life. Collected or donor blood is usually stored as separate components and some components have short shelf life. For example, there are no storage solutions to keep platelets beyond seven days. Red blood cells, the most frequently used component, has a shelf life of 35 to 42 days at refrigerated temperatures. This limited shelf life makes it difficult if not impossible to have a stockpile of red blood cells for a natural disaster or an unusual demand for a particular blood type as for example "O" types.

Over the past 20 years there have been a number of approaches for extending the shelf life of red blood cells. For example, a U.S. Pat. No. 5,030,200 of Judy et al. discloses a method for eradicating infectious biological contaminants in body tissues. As disclosed, the method eradicates infectious pathogenic contaminants such as enveloped viruses, bacteria, trypanosomal and malarial parasites, present in body tissues, such as blood, blood components, semen, skin, and cornea, before the treated body tissues are introduced into, or transplanted onto, the body of a human. Such method includes the steps of (1) admixing an effective non-toxic amount of photoactive compound which has selectivity for binding to the infectious pathogenic biological contaminants present therein with the body tissues outside the body to produce resulting body tissues; (2) maintaining the resulting body tissues in a suitable container; and (3) irradiating the resulting body tissues in the container for an effective period of time with an effective level of radiation. The radiation penetrates the resulting body tissues and eradicates the photoactive-compound-bound contaminants present in the resulting tissue. In essence, it produced a decontaminated body tissue suitable for introducing into or transplanting onto the body of a human.

A more recent U.S. Pat. No. 5,476,764 of Bitensky discloses a method using CO for extending the useful shelf life of refrigerated red blood cells. The method uses carbon monoxide for stabilizing hemoglobin in red blood cells to be stored at low temperatures. Changes observed in the stored cells are similar to those found in normal red cells aging in the body. The extent thereof being directly related to the duration of refrigerated storage. Changes in cell buoyant density, vesiculation, and the tendency of stored cells to bind autologous IgG antibody directed against polymerized band 3 IgG, all of which are related to red blood cell senescence have been substantially slowed when red blood cells are treated with CO. Removal of the carbon monoxide from the red blood cells is readily and efficiently accomplished by photolysis in the presence of oxygen so that the stored red blood cells may be safely transfused into a recipient.

Finally, a U.S. Pat. et al. No. 7,717,274 of Kao discloses a Device and Method for Preparing Washed Red Blood Cells for New Born Transfusions. As disclosed a newborn transfusion cell washing device generally comprises a disposable, graduated test tube shaped container having a cap with an inlet port, an injection/sampling port, a suction port, and a vent. The container is capable of being inserted into a conventional clinical centrifuge. The device requires a relatively small volume to operate, 25 ml or less per procedure and can be performed easily by any hospital blood bank technologist without any specific training. Washed red blood cells can be provided to the patient in a timely manner without the need for "fresh blood." Any in-dated red blood cells can be washed to remove excessive potassium and other toxins. The main red blood cells aliquot can be saved and repeatedly sampled until the unit is expired or exhausted. This provides a cost savings to the hospital and more importantly, minimizes the recipient's donor exposure. Kao et al also discloses storing red blood cell products using chemical antioxidants to extend the shelf life from 35 days to 42 days.

Notwithstanding the methods above, it is presently believed that there is a need and a potential commercial market for the present invention and for a method to extend the shelf life of red blood cells by up to as much as about 66%. It is also believed that the procedure for extending the shelf life of red blood cells can be readily completed by any hospital blood bank technology without any special skills and does not require excessive cost for equipment.

SUMMARY OF THE INVENTION

In essence, the invention contemplates a method for enhancing the shelf life of donor blood from about 39 days to 65 days (shelf life increase of as much as 66%). The method comprises or consists of the following steps. In a first step, the blood is transferred into a standard sterile container coated with an anticoagulant (as for example Ethylenedaiminetetraacetic Acid (EDTA), heparin or the like and mixtures thereof). In a second step, the vial containing blood and anticoagulant is placed in a centrifuge and rotated at between about 3,000 to 5,000 rpm and preferably at about 4,000 rpm for about 15 minutes. After centrifuging the red blood cells are separated from the remaining matter and placed in a sterile tube. In the next step, the red blood cells are irradiated by a laser that emanates a wavelength of between 350 nm and 1,000 nm preferably at 633 nm for a time period of between 16 and 32 hours, preferably about 24 hours on both sides. Frequent rotation is used to irradiate each side to obtain uniform exposure.

The invention also comprises or consists of an enhanced donor blood that has a shelf life that has been extended up to about 66%.

The invention will now be described in connection with the following drawings.

DESCRIPTION OF THE PREFERRED EMBODIMENTS OF THE INVENTION

Figure 1:
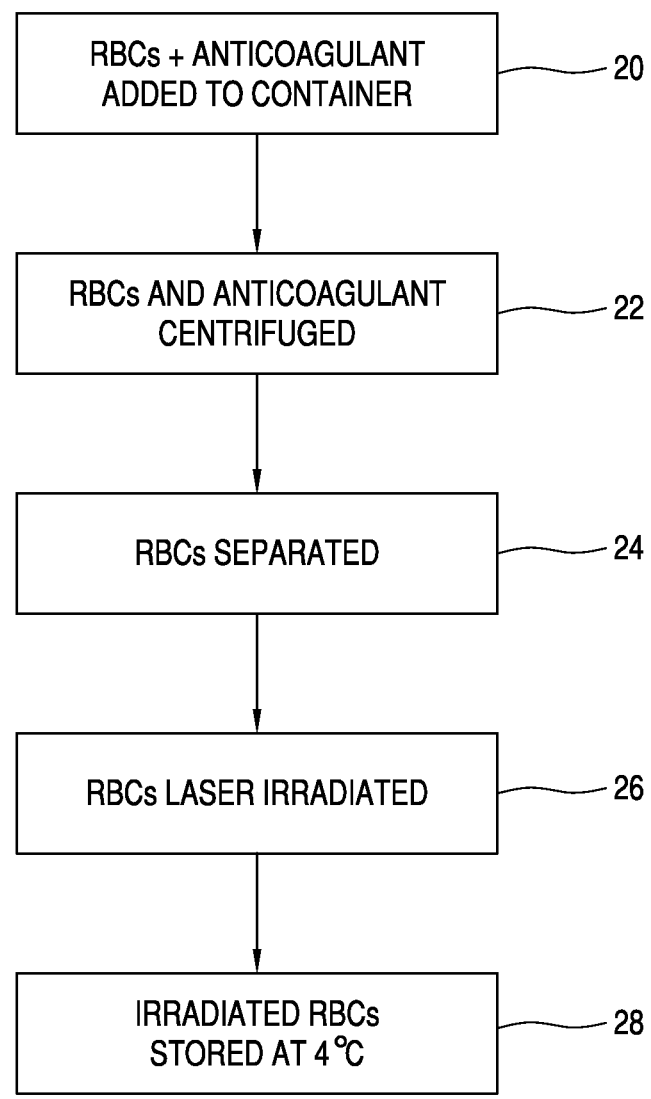
FIG. 1 is a flowchart illustrating the procedure for extending the shelf life of donor blood.

Blood, the circulating tissue is the life saving fluid in the body and it has the most essential function of supplying oxygen and removing $CO_2$ from every part of the body. There are blood banks all over the world for collecting this vital fluid from donors for transfusion into the acceptors (during major surgery or in trauma care). The variety of blood samples collected should be stored for quite a long time for effective use. It is important to note that the blood stored up to a maximum of 42 days only can be administered to the acceptor according to the USA federal law. This is because red blood cells spoil due to slow hemolysis and release of nitric oxide NO which leads to some complications to the acceptor.

In this line, a number of efforts have been taken to enhance the storage or shelf life of collected blood. For example, tirilazd mesylate (TM), a powerful antioxidant has been used to protect the stored red blood cells against the oxidative damage. It increases the osmotic fragility and hence stored shelf life. Another interesting work was the effect of magnetic field in improving the erythrocyte osmotic fragility. An improvement by 15% has been observed for a magnetic field of 0.15 T for 30 minutes.

For the same objective the Applicants have made use of low power laser irradiation instead of chemical or magnetic field interaction.

Fresh blood (5 ml) was taken from the blood bank of King Khalid University Hospital (KKUH), Diria, Riyadh and transferred into a violet standard vial containing a standard concentration of EDTA as an anticoagulant. This was centrifuged at 4000 rpm for 15 minutes which put the red blood cells at the bottom, leaving white blood cells and platelets as a grey puffy mass, and a yellow-green liquid plasma above the puffy mass. Applicant removed all except the red blood cells (of about 2 ml) left at the bottom. This was the experimental sample. Red blood cells, placed in a closed, sterile tube, was irradiated on both sides with the laser (He Ne laser of $\lambda$=633 nm of measured power of 690 microwatt over a diameter of 3 mm) and the irradiation was for 24 hours, with frequent rotation of the tube for uniform exposure. This corresponded to an irradiance of 7.6 mW/cm$^2$ and a fluence of 59 J. The irradiated and control samples were kept at 4° C. in a refrigerator. The osmotic fragility (OF) of above both sets of samples were monitored using absorption at 540 nm according to the well established protocol.

Such measurements were done for every six days for the control and laser irradiated samples. The instrument used was the Perkin Elmer UV Vis spectrometer which has a scan range 200 to 800 nm.

The osmotic fragility of the blood is in proportion to the degradation of red blood cells, as measured by the absorption spectra at 540 nm. This is because the absorption peak at 540 nm is most sensitive to monitor the spectral feature of hemoglobin, more precisely the porphyrin in the heme part of the red blood cells. The area of absorption at 540 nm is a measure of decomposition of red blood cells. It could be seen that there was about a 53% retardation in the hemolysis of the red blood cells in comparison to the control, un-irradiated sample.

Figure 2:
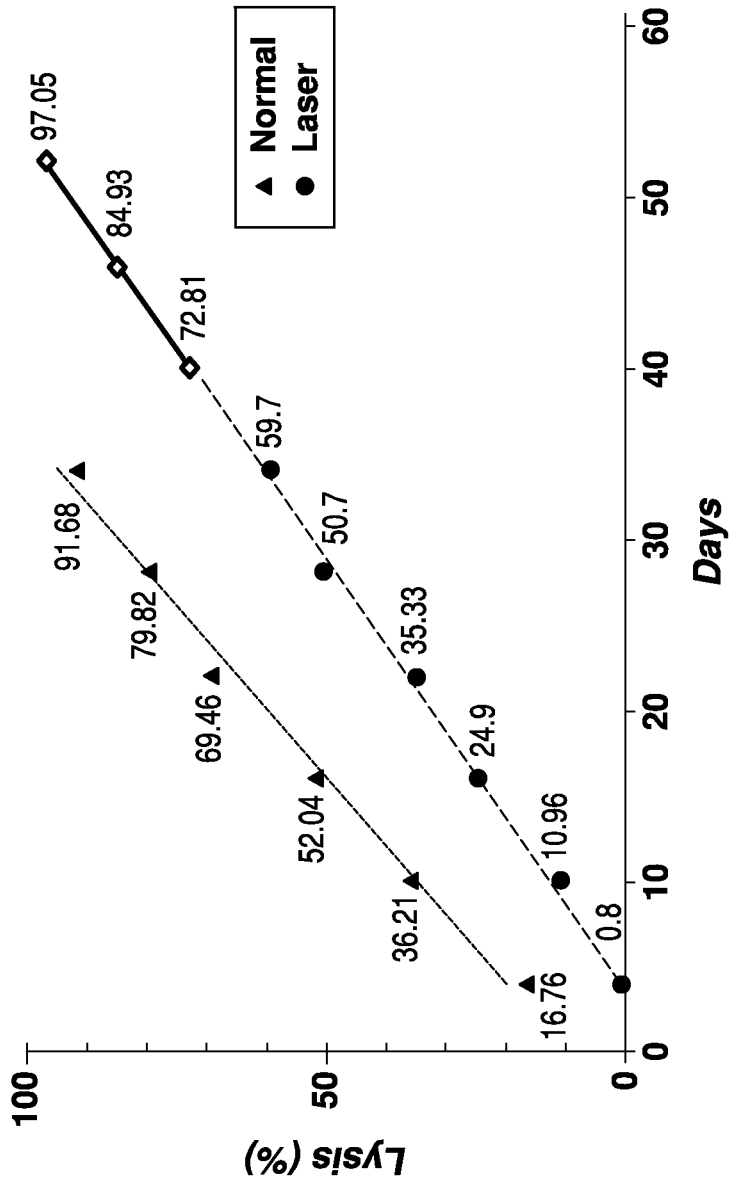
FIG. 2 is a graphical representation of the percentage of hemolysis as a function of time for a laser irradiated and an untreated control sample.

Half life is defined as 50% hemolysis and it was about 18 days for the control while it is 30 days for the laser irradiated sample. That amounts to about a 66% enhancement in shelf life of donor blood due to the laser bio stimulation. This is shown in FIG. 2 which represents the percentage of hemolysis as a function of time for the laser irradiated and un-irradiated control sample.

As illustrated in FIG. 1, a method for laser enhancing the shelf life of donor blood from the normally acceptable 35 to 42 days to as much as 58 to about 70 days is shown. The method comprises the following steps. In a first step 20 the blood is transferred into a sterile container having an anticoagulant as for example (EDTA), heparin or the like and perhaps mixtures thereof. In a second step 22, the blood and anticoagulant is placed in a centrifuge and rotated at between 3,000 to 5,000 rpm for about 15 minutes. In a third step 24, after centrifuging the red blood cells are separated from the remaining matter and placed in a sterile tube. In the next step 26 the red blood cells are irradiated by a laser that emits a wavelength of between about 350 nm and 1,000 nm and preferably at 633 mm for a time period of between 16 and 32 hours preferably about 24 hours. Frequent rotation of the tube is used to irradiate the red blood cells uniformly. The irradiation of red blood cells wherein the red blood cells were irradiated on both sides with frequent rotation of the tube at about 7.6 mW/cm$^2$ and a fluence of 59 J and storage at about 4° C. in step 28 appears to provide an extended storage period.

While the invention has been described in connection with its preferred embodiments it should be recognized that changes and modifications may be made therein without departing from the scope of the appended claims.

What is claimed is:

1. A method for laser enhancing the shelf life of donor blood, said method comprising the steps of:
    transferring the donor blood into a sterile container with an anticoagulant in which the anticoagulant is selected from the group consisting of ethylenedaiminetetraacetic acid (EDTA), heparin and a mixture thereof and in which the centrifuge is rotated about 4000 rpm for a period of about 15 minutes; in which the anticoagulant EDTA and in which the laser emanates a wavelength of between about 350 nm and about 400 nm at a power level of between about 400 btw and about 1000 btw;
    centrifuging the blood and anticoagulant at about 3000 to about 5000 rpm for between about 10 to about 20 minutes;
    separating the red blood cells from the remaining matter and placing the red blood cells in a sterile tube;
    irradiating the red blood cells with a laser emanating a wavelength of between about 350 nm and about 1000 nm for a period of between about 16 and about 32 hours; and
    preserving the red blood cells in cold storage.

2. A method for laser enhancing the shelf life of donor blood according to claim 1, in which the method further comprises the use of EDTA as the anticoagulant in a standard vial with a standard concentration of EDTA.

3. A method for laser enhancing the shelf life of donor blood according to claim 2, wherein the laser is a HeNe laser and the blood is irradiated with a wavelength of 633 nm for about 24 hours.

4. A method for laser enhancing the shelf life of donor blood according to claim 3, wherein the radiation is 7.6 mW/cm$^2$ and a fluence of about 59 J.

5. A method for laser enhancing the shelf life of donor blood according to claim 4, in which the red blood cells are rotated during the 24 hours of irradiation to expose both sides of the red blood cells for uniform exposure.

6. A method for laser enhancing the shelf life of donor blood, said method consisting of the following steps:

transferring the donor blood into a sterile container with a predetermined amount of ethylenedaiminetetraacetic acid (EDTA) per unit of blood in which the blood and ethylenedaiminetetraacetic acid has been centrifuged at about 4,000 rpm for about 15 minutes; the red blood cells have been separated from the remaining matter and placed in a sterile tube; and irradiated on both side with 633 nm wavelength of light for about 24 hours;

centrifuging the blood and EDTA at about 4000 rpm for about 15 minutes;

separating the red blood cells from the remaining matter and placing the red blood cells in a sterile tube;

irradiating the red blood cells with a laser emanating a wavelength of 633 nm with a measured power of about 690 μw over a diameter of about 3 mm for about 24 hours; and subjecting the RBCs to refrigerated cold storage at about 4° C.

\* \* \* \* \*